US010639252B2

(12) United States Patent
Colvan et al.

(10) Patent No.: US 10,639,252 B2
(45) Date of Patent: May 5, 2020

(54) COMPOSITIONS FOR SKIN EXFOLIATION AND USE THEREOF

(75) Inventors: Lora Colvan, Carlsbad, CA (US);
Rahul Mehta, San Marcos, CA (US);
Sujatha Sonti, San Marcos, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/243,567

(22) Filed: Sep. 23, 2011

(65) Prior Publication Data
US 2013/0074860 A1 Mar. 28, 2013

(51) Int. Cl.
A61K 8/365 (2006.01)
A61K 8/368 (2006.01)
A61K 8/67 (2006.01)
A61Q 19/00 (2006.01)
A61Q 19/10 (2006.01)
A61Q 19/08 (2006.01)

(52) U.S. Cl.
CPC .............. A61K 8/365 (2013.01); A61K 8/368 (2013.01); A61K 8/671 (2013.01); A61Q 19/00 (2013.01); A61Q 19/08 (2013.01); A61Q 19/10 (2013.01); A61K 2800/28 (2013.01)

(58) Field of Classification Search
None
See application file for complete search history.

(56) References Cited

U.S. PATENT DOCUMENTS

| 3,932,665 | A | * | 1/1976 | Van Scott et al. | 514/703 |
| 4,608,370 | A | * | 8/1986 | Aronsohn | 514/159 |
| 5,133,967 | A | * | 7/1992 | Smith | 424/401 |
| 5,505,948 | A | * | 4/1996 | Rapaport | 424/401 |
| 5,527,530 | A | * | 6/1996 | Simmons et al. | 424/401 |
| 5,728,732 | A | * | 3/1998 | Corey | A61K 8/37 |
| | | | | | 514/544 |
| 5,730,991 | A | | 3/1998 | Rapaport | |
| 5,997,889 | A | | 12/1999 | Durr et al. | |
| 6,015,568 | A | | 1/2000 | Segot et al. | |
| 6,281,250 | B1 | * | 8/2001 | Shealy | 514/683 |
| 6,358,517 | B1 | | 3/2002 | Pillai et al. | |
| 6,782,307 | B2 | | 8/2004 | Wilmott et al. | |
| 6,869,611 | B1 | | 3/2005 | Kligman et al. | |
| 2003/0165546 | A1 | | 9/2003 | Resch et al. | |
| 2003/0215413 | A1 | * | 11/2003 | Fares | A61K 8/342 |
| | | | | | 424/70.16 |
| 2003/0232091 | A1 | * | 12/2003 | Shefer et al. | 424/490 |
| 2004/0034098 | A1 | | 2/2004 | Varani et al. | |
| 2004/0096419 | A1 | * | 5/2004 | Golz-Berner | A61K 8/11 |
| | | | | | 424/74 |
| 2005/0013784 | A1 | * | 1/2005 | Trigg et al. | 424/62 |
| 2006/0051429 | A1 | * | 3/2006 | Murad | 424/616 |
| 2006/0110416 | A1 | * | 5/2006 | Ryles | A61K 8/0212 |
| | | | | | 424/401 |
| 2006/0263398 | A1 | | 11/2006 | Kalil | |
| 2007/0025949 | A1 | | 2/2007 | Hansenne et al. | |
| 2009/0004280 | A1 | | 1/2009 | Marion | |
| 2009/0131375 | A1 | * | 5/2009 | Gross | A61K 8/0208 |
| | | | | | 514/159 |
| 2009/0196926 | A1 | * | 8/2009 | De Rosa | A61K 8/25 |
| | | | | | 424/484 |
| 2010/0255079 | A1 | | 10/2010 | Sanmiguel et al. | |

FOREIGN PATENT DOCUMENTS

| CA | 2164229 C | 4/2008 | |
| EP | 0631772 B1 | 8/1999 | |
| EP | 1759688 A1 * | 3/2007 | ............. A61K 8/368 |
| ES | S2255862 B1 | 7/2007 | |
| KR | 10-2004-0043703 A | 5/2004 | |
| KR | 20050028544 A * | 3/2005 | |
| WO | WO9728786 A1 | 8/1997 | |
| WO | WO9746221 A1 | 12/1997 | |
| WO | WO 02/28361 * | 4/2002 | |
| WO | WO-02092560 A1 * | 11/2002 | ........... C07C 403/08 |
| WO | WO2006-028361 A1 | 3/2006 | |

OTHER PUBLICATIONS

Truth in Aging website article "Panthenol" dated May 15, 2009 http://www.truthinaging.com/ingredients/panthenol.*
Herbig et al. "Combination of Jessner's Solution and Trichloroacetic Acid Chemical Peel: technique and outcomes," Plastic and Reconstructive Surgery Journal 124(3):955-964, 2009.*
Linder "Superficial chemical peeling: minimal effort, maximal results," dermatologist.com 19(4), Apr. 2011.*
Kristy "Skin Medica chemical peels: Illumize, vitalize, Rejuvenize," bestofbothworldsaz.com.*
David "Easy Mondays: SD Alcohol: what is it?" truthinskincare.com, Jan. 21, 2008.*
Peikert et al. "The efficacy of various degreasing agents used in trichloroacetic acid peels," Journal of Dermatologic Surgery and Oncology 20:724-728, 1994.*
Monheit "Chemical peels," medscape.com Skin Therapy Letter 9(2), 2004.*
Fischer et al. "Chemical peels in aesthetic dermatology: an update 2009," Journal of the European Academy of Dermatology and Venereology 24:281-292, 2010.*
Machine translation EP 1759688, printed 2015.*

(Continued)

Primary Examiner — David J Blanchard
Assistant Examiner — Alissa Prosser
(74) Attorney, Agent, or Firm — Matthew O. Brady

(57) ABSTRACT

The present invention provides a skin peel composition including a plurality of substances, such as lactic acid, salicylic acid, and resorcinol and, additionally a post-inflammatory hyper pigmentation reducing substance such as a retinol (vitamin A) or retinol derivative. Skin is first prepared using an alcohol preparation followed by a combinations of acids and, lastly, a retinol or retinol derivatives. Other agents such as ascorbic acid (vitamin C) and vitamin E can be added as needed. Application of the skin peel composition may be either topically in the form of a cream or gel, and may further be injected subcutaneously into the skin to achieve deeper penetration of the composition within the skin layers of the area to be treated.

1 Claim, 5 Drawing Sheets

(56) References Cited

OTHER PUBLICATIONS

Darlenski et al. "Topical retinoids in the management of photodamaged skin: from theory to evidence-based practical approach," British Journal of Dermatology 163:1157-1165, 2010.*
Yan et al. "Levels of retinyl palmitate and retinol in the skin of SKH-1 mice topically treated with retinyl palmiate and concomitant exposure to simulated solar light for thirteen weeks," Toxicology and Industrial Health 23:581-589, 2007.*
Gupta et al. "Lustra®, Lustra-AF® and Alustra™," Skin Therapy Letter 8(5):1-3, Jun. 2003.*
Handbook of Dermatological Drug Therapy, p. 336, accessed 2018.*
BASF AG: "Retinol", May 1, 2005, pp. 1-10, Retrieved from the Internet, http://www.dr-baumann-international.co.uk/science/BASF%20Vitamin%20A.pdf.
BESTOFBOTHWORLDSAZ-Exfoliation. Dec. 30, 2010, p. 3-11, http://web.archive.org/web/20101230064257/http://bestofbothworldsaz.com/tag/exfoliation.

European Patent Office Communication, European Search Report, dated May 15, 2015, Reference 172 278 a/scho, Application No. 12833417.4.-1548, 13 pages.
Hexsel, et al., Microdermabrasion followed by a 5% retinoid acid chemical peel vs. a 5% retinoid acid chemical peel for the treatment of photoaging—a pilot study, Journal of Cosmetic Dermatology, 2005, vol. 4, Blackwell Publishing, pp. 111-116.
Landau, M., Chemical Peels, Clinics in Dermatology, Mar. 2008, pp. 200-208, vol. 26, Issue 2, Elsevier.
Notification of Transmittal of International Search Report and the Written Opinion of the International Searching Authority, or the Declaration, dated Dec. 18, 2012, International Application No. PCT/US2012/056681, International Filing Date Sep. 21, 2012, Applicant: SkinMedica, Inc., 12 pages.
REALSELF-Applying Acetone 100% Necessary Before Vi Peel?,Sep. 3, 2011, http://web.archive.org/web/20110903100503/http://www.realself.com/question/vi-peel-acetoneapplication, 2 pages.

* cited by examiner

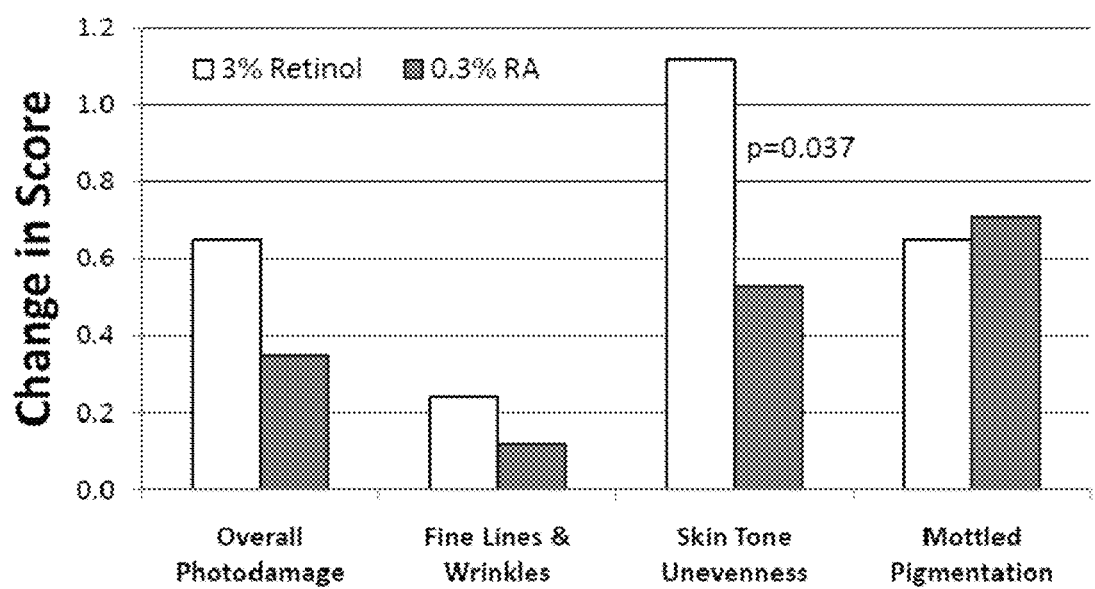

COMPOSITIONS FOR SKIN EXFOLIATION AND USE THEREOF

BACKGROUND OF THE INVENTION

A variety of skin problems including acne, scars, pigmentation disorders, sun exposure, etc., have led to the development of a variety of compositions and therapies directed toward their treatment. Such treatments may include skin creams, lotions, or ointments which are applied to help rejuvenate or nourish the underlying skin layers. An additional treatment includes the application of a compound, which aids in the removal of damaged skin layers (i.e., a skin peel agent).

Skin peels generally include one or more acidic components which are applied to the skin in order to remove a layer of the skin. The removal of a layer of skin allows a new layer of skin lining to develop, often resulting in evenly colored, healthier skin and further reducing the skin problems. Depending on the level of existing skin conditions a patient has, increased acidic concentrations or prolonged application of a skin peel composition may be implemented in order to treat deeper skin layers or severe cases of skin disorders.

SUMMARY OF THE INVENTION

Provided herein are skin peel compositions which are available without the need for a prescription, which has a reliable concentration for treatment of patients, provides for rapid therapeutic results faster than that of known skin peel compositions, which reduces pain and discomfort, substantially reduces any preparation time or down-time, and further provides therapeutic results faster than that of known skin peel compositions.

The present disclosure relates to dermatological compositions and methods for application thereof, and in particular compositions for efficiently and effectively performing chemical peel procedures. The goal is to provide patients with a consistent, single-source for exfoliation procedures that will ensure predictable results and improve ordering convenience for medical professionals.

Chemical peeling can be done in varying degrees of depth. A very superficial peel (exfoliation) is generally one which is comparatively superficial in effect in which the peel thins and/or removes the stratum corneum and does not extend below the stratum granulosum. Superficial peels (epidermal) peels are those that remove part or all of the epidermis extending from the stratum granulosum to the basal cell layer. Medium (papillary dermis) peels are those that remove all of the epidermis and part/all of the papillary dermis. Lastly, deep (reticular dermis) peels are those that remove the papillary dermis down to the upper portion of the reticular dermis.

The use of the methods described herein may provide one or more benefits to the skin of the user undergoing chemical peels. For example, a patient undergoing chemical peels may observe perioral fine wrinkle improvement, periocular fine wrinkle improvement, hyperpigmentation improvement, hypopigmentation improvement, tactile roughness improvement, sallowness improvement, acne scarring improvement, improvement in photodamage, improvement in skin tone unevenness, improvement in mottled pigmentation and/or increased overall skin quality. Additionally, a patient undergoing chemical peels employing the methods described herein may not experience a worsening of erythema.

The present disclosure provides a skin peel composition including a plurality of substances, such as lactic acid, salicylic acid, and resorcinol and, additionally a post-inflammatory hyper pigmentation reducing substance such as retinol. In some embodiments, the post-inflammatory hyper pigmentation reducing substance may also include retinal, retinaldehyde, retinyl palmitate, retinyl acetate, and other derivatives of vitamin A. Compositions for use in the present methods include those that are prepared directly from pure powder or crystals rather than purchasing a pre-made solution from a chemical supplier. Retinol (vitamin A; (2E,4E,6E,8E)-3,7-dimethyl-9-(2,6,6-trimethylcyclohex-1-enyl)nona-2,4,6,8-tetraen-1-ol) sold in lipid base is commercially available from BASF, but the inventors determined that this commercially available product was not as effective in the methods described herein as powdered substantially purified retinol dissolved in alcohol.

Further, the present retinol compositions can be prepared at least a 3% concentration for a very superficial peel or at least a 5% concentration for a superficial peel.

Provided herein is a method for exfoliation of skin, the method comprising: cleansing skin to be exfoliated; applying an acidic solution to the skin; and applying a retinol solution to the skin; wherein said retinol solution is applied to the skin after the acidic solution is applied to the skin. A benefit of the present exfoliation processes disclosed herein is that additional neutralization of skin is not required after application of the acidic solution.

Provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin.

Provided herein is a method for exfoliation of skin, the method comprising: cleansing skin to be exfoliated; applying an acidic solution to the skin; and applying a retinol solution to the skin; wherein said retinol solution is applied to the skin after the acidic solution is applied to the skin. A benefit of the present exfoliation processes disclosed herein is that additional neutralization of skin is not required after application of the acidic solution.

Provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin.

In certain embodiment, the present retinol compositions can be prepared at least a 3% concentration for a very superficial peel or at least a 5% concentration for a superficial peel.

A benefit of the present exfoliation processes disclosed herein is that additional neutralization of skin is not required after application of the acidic solution. In one embodiment, the method improves overall photodamage. In another embodiment, the method improves fine lines and wrinkles. In yet another embodiment, the method improves skin tone unevenness. Improvement in skin after treatment with retinols as described herein in such methods can be, for example, at least 1.5 fold, at least 2-fold, at least 3-fold, at least 4-fold, at least 5-fold or more compared to untreated skin. Improvement in skin after treatment with retinol as described herein in such methods can be, for example, at least 1.5 fold or at least 2-fold compared to treatment methods with retinoic acid.

Skin can be cleansed with an appropriate solution such as an alcoholic solution. A non-limiting example of an alcohol to be used in such a solution includes, but is not limited to isopropyl alcohol.

An acidic solution to be used in the methods described herein includes any acid or combination of acids that sufficiently exfoliate the superficial dermis and/or epidermis. The acidic solution can contain one or more of lactic acid, salicylic acid, resorcinol, glycolic acid, malic acid, mandalic acid, citric acid, Trichloroacetic acid (TCA), phenol, tartaric acid, or a combination thereof. In one embodiment, the acidic solution comprises lactic acid, salicylic acid, and resorcinol. In another embodiment, the acidic solution further comprises Isoceteth-20.

Retinol solutions can be applied once skin has dried after application of the acidic solution. Further, retinol solutions can be applied once, or more than one time following application of the acidic solution based upon the condition of the skin to be treated. For example, a retinol solution can be applied to the skin from about 3 minutes to about 1 week after application of the acidic solution. In one embodiment, a retinol solution is applied to the skin about 3 minutes after application of the acidic solution. In another embodiment, a retinol solution is applied to the skin about 3 minutes after application of the acidic solution and then every day for about 1 week.

Retinol solutions are to be prepared directly from a pure chemical powder in a concentration of at least 3% or at least 5%. In one embodiment, a retinol solution has a purity of at least about 98% and a concentration of at least 3% or at least 5%. In other embodiment, a retinol solution has a concentration of about 3% or about 5%. In yet another embodiment, a retinol solution has a concentration of at least 3%, at least 4%, at least 5%, at least 6%, at least 7%, at least 8%, at least 9%, or at least 10% or more.

In some cases, the acidic solution and/or the retinol solution can further contain one or more adjuvants.

In other embodiments, retinaldehyde, retinal, retinyl palmitate, retinyl acetate or other retinoid derivatives may also be used. In one embodiment, retinaldehyde, retinal, retinyl palmitate, retinyl acetate or other retinoid derivative is in a concentration of at least 3%, at least 4%, at least 5%, at least 6%, at least 7%, at least 8%, at least 9%, at least 10% or more. In one embodiment retinaldehyde, retinal, retinyl palmitate, retinyl acetate or other retinoid derivative is in a concentration of about 5% in the solution. In another embodiment, retinaldehyde, retinal, retinyl palmitate, retinyl acetate or other retinoid derivative is in a concentration of about 3% in the solution. In some instances, the retinaldehyde, retinal, retinyl palmitate, retinyl acetate or other retinoid derivative solution lacks surfactants, stabilizers, or lacks surfactants and stabilizers.

Using the compositions described herein, at least about 10%, at least about 15%, at least about 20%, at least about 25%, at least about 30%, at least about 40%, at least about 50%, at least about 60%, at least about 70%, at least about 80%, or at least about 90% of the treated skin is exfoliated. In one embodiment, all or part of the superficial dermis is exfoliated. In another embodiment, all or part of the epidermal is exfoliated.

The present methods can further include application of one or more of sunblock, moisturizer, emollient, anti-oxidant, astringents to the skin prior to the cleansing step or subsequent to application of the retinol solution.

Provided herein is a composition for use in a skin exfoliation treatment described herein comprising one or more of lactic acid, salicylic acid, resorcinol, glycolic acid, malic acid, mandalic acid, citric acid, Trichloroacetic acid (TCA), phenol, tartaric acid, or a combination thereof. In one embodiment, the acidic solution comprises lactic acid, salicylic acid, and resorcinol. In another embodiment, the acidic solution may further contain isoceteth-20, panthenol, denatured alcohol, or a combination thereof.

Provided herein is a composition for use in a skin exfoliation treatment described herein comprising about 3% or about 5% of retinol. In one embodiment, the composition is prepared using a pure powder comprising said retinol. In another embodiment, the composition does not contain a surfactant, a stabilizer, or both.

Provided herein are kits for exfoliating skin comprising: a skin cleanser; an acidic solution; a retinol solution; and instructions for applying solutions, where each of the kit components has been described supra.

Provided herein is a method for exfoliation of skin, the method comprising cleansing skin to be exfoliated; applying an acidic solution to the skin; and applying about a 3% retinol solution to the skin; wherein the retinol solution is applied to the skin after the acidic solution is applied to the skin.

Provided herein is a method for exfoliation of skin, the method comprising cleansing skin to be exfoliated; applying an acidic solution to the skin; and applying about a 3% retinol solution to the skin; wherein the retinol solution is applied to the skin after the acidic solution is applied to the skin and wherein the solution does not contain a surfactant or a stabilizer.

Provided herein is a method for exfoliation of skin, the method comprising cleansing skin to be exfoliated; applying an acidic solution to the skin; and applying about a 5% retinol solution to the skin; wherein said retinol solution is applied to the skin after the acidic solution is applied to the skin.

Provided herein is a method for exfoliation of skin, the method comprising cleansing skin to be exfoliated; applying an acidic solution to the skin; and applying about a 5% retinol solution to the skin; wherein said retinol solution is applied to the skin after the acidic solution is applied to the skin and wherein said solution does not contain a surfactant or a stabilizer.

Provided herein is a method for exfoliation of skin, the method comprising cleansing skin to be exfoliated with an isopropyl alcohol solution; applying an acidic solution comprising lactic acid, salicylic acid, and resorcinol to the skin; and applying a 5% retinol solution to the skin; wherein said retinol solution is applied to the skin after the acidic solution is applied to the skin and wherein said solution does not contain a surfactant or a stabilizer. In one embodiment, the acidic solution further comprises isoceteth-20, Panthenol, denatured alcohol, or a combination thereof.

Provided herein is a method for exfoliation of skin, the method comprising cleansing skin to be exfoliated; applying an acidic solution to the skin; and applying about a 3% retinol solution to the skin; wherein the retinol solution is applied to the skin after the acidic solution is applied to the skin.

Provided herein is a method for exfoliation of skin, the method comprising cleansing skin to be exfoliated; applying an acidic solution to the skin; and applying about a 3% retinol solution to the skin; wherein the retinol solution is applied to the skin after the acidic solution is applied to the skin and wherein the solution does not contain a surfactant or a stabilizer.

Provided herein is a method for exfoliation of skin, the method comprising cleansing skin to be exfoliated; applying an acidic solution to the skin; and applying about a 5% retinol solution to the skin; wherein said retinol solution is applied to the skin after the acidic solution is applied to the skin.

Provided herein is a method for exfoliation of skin, the method comprising cleansing skin to be exfoliated; applying an acidic solution to the skin; and applying about a 5% retinol solution to the skin; wherein said retinol solution is applied to the skin after the acidic solution is applied to the skin and wherein said solution does not contain a surfactant or a stabilizer.

Provided herein is a method for exfoliation of skin, the method comprising cleansing skin to be exfoliated with an isopropyl alcohol solution; applying an acidic solution comprising lactic acid, salicylic acid, and resorcinol to the skin; and applying a 5% retinol solution to the skin; wherein said retinol solution is applied to the skin after the acidic solution is applied to the skin and wherein said solution does not contain a surfactant or a stabilizer. In one embodiment, the acidic solution further comprises isoceteth-20, Panthenol, denatured alcohol, or a combination thereof.

In yet other embodiments, retinaldehyde, retinal, retinyl palmitate, retinyl acetate or other retinoid derivatives may also be used in the exfoliation of skin. In one embodiment, retinadehyde, retinal, retinyl palmitate, retinyl acetate or other retinoid derivative is in a concentration of at least 3% or at least 5% or more. In one embodiment retinaldehyde, retinal, retinyl palmitate, retinyl acetate or other retinoid derivative is in a concentration of about 5% in the solution. In another embodiment, retinaldehyde, retinal, retinyl palmitate, retinyl acetate or other retinoid derivative is in a concentration of about 3% in the solution. In some instances, the retinaldehyde, retinal, retinyl palmitate, retinyl acetate or other retinoid derivative solution lacks surfactants, stabilizers, or lacks surfactants and stabilizers.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the disclosure are set forth with particularity in the appended claims. A better understanding of the features and advantages of the present compositions, kits and methods will be obtained by reference to the following detailed description that sets forth illustrative embodiments, in which the principles of the disclosure embodiments are utilized, and the accompanying drawings of which:

FIG. 8 provides the results of an independent assessment of efficacy post-peel #3 based on blinded photograph evaluation by an expert physician. Retinol treatment produced about twice as much improvement in photodamage, fine lines and wrinkles and unevenness of skin tone as retinoic acid. Improvement in skin tone unevenness following treatment with 5% Retinol was statistically significant compared to 0.3% Retinoic Acid.

DETAILED DESCRIPTION OF THE INVENTION

Figure 1:
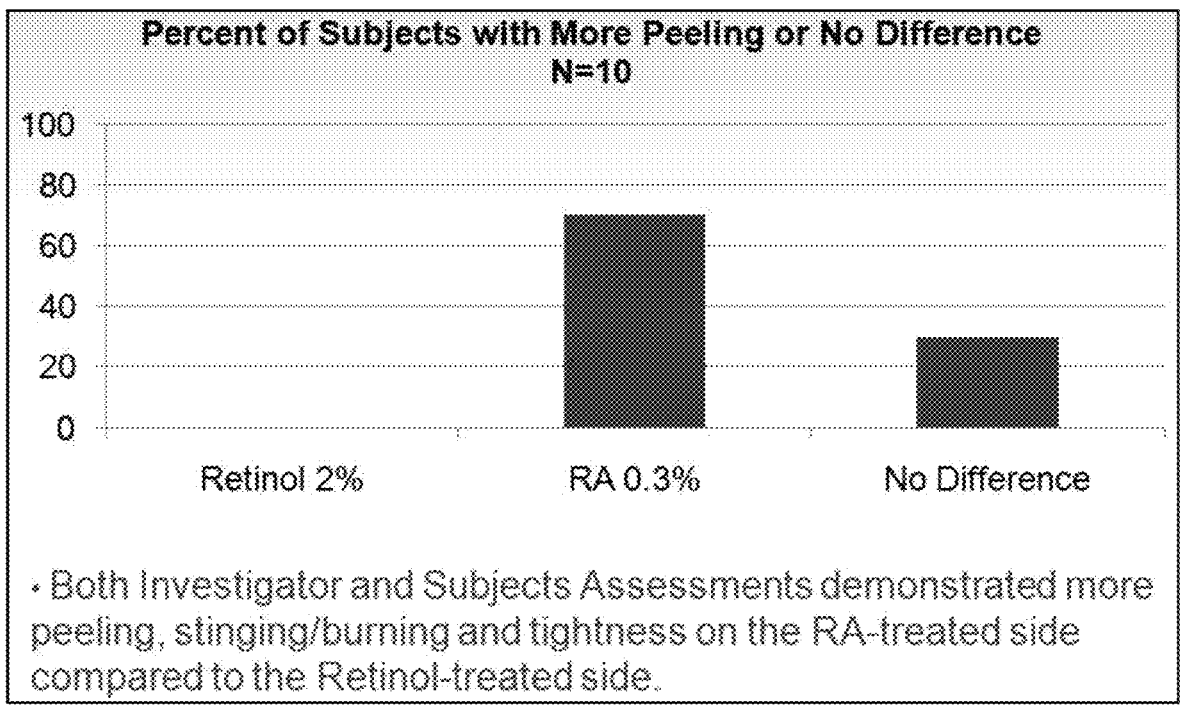
FIG. 1 illustrates the results of Study 1 (investigator and subject assessments; peeling efficacy and tolerability). Results are shown as percentage of subjects preferring each indicated treatment or no difference.

While beneficial in some regard, skin peels can have negative side effects. Depending on the particular acidic component used, the removal of a skin layer may result in post inflammatory hyper pigmentation (PIH), which appears as variations in skin pigmentation, i.e., lighter or darker patches on the skin area treated. In order to prevent or reduce such pigmentation complications, the skin area to be treated may need several applications of additional preparatory compositions prior to the application of the skin peel itself. Such repeated preparatory applications may extend over many weeks before the skin can finally be subjected to the skin peel in an attempt to minimize the likelihood of experiencing pigmentation abnormalities. Furthermore, subsequent to being treated, a patient may wish to reduce social interaction due to the appearance of the peeling skin in the days following the skin peel application. Also, depending on the depth of treatment, the patient may even experience some pain and discomfort. The combination of the preparation of the skin prior to the application of the skin peel and the down-time resulting after treatment prolongs the amount of time required for a successful skin peel treatment, thereby burdening and inconveniencing a patient.

Retinoic Acid (commonly known as Retin-A®) can be employed to combat skin disorders such as acne and has also been used to reduce the appearance of wrinkles and aging in the skin due to prolonged sun exposure. However, Retinoic Acid also appears to inhibit melanin synthesis, which is an underlying cause of PIH. PIH often appears subsequent to skin peel procedures as blotchy skin, i.e., areas of the skin surface having variations in pigment. Treatment with Retinoic Acid currently requires a prescription from a doctor; although prescriptions are formulated for a final concentration of 0.3%, the prescriptions are not reliable at this concentration and in many cases, the final concentration is below the prescribed amount. When using Retinoic Acid for skin exfoliation procedures, medical professionals must order the solution from a pharmacy and variations within prescriptions leads to variations in the outcome of the exfoliation procedure.

The compositions of the present disclosure are useful in reducing fine wrinkles and lines, reducing pore size, exfoliating the skin, reducing or eliminating acne, toning the skin, enhancing the skin's radiancy, and providing softer, smoother skin with a more uniform appearance. The compositions may also increase uniformity and consistency in results achieved as compared to other skin exfoliation compositions and procedures, including retinoic acid-containing exfoliation solutions.

All percentages and ratios used herein are by weight of the total composition and all measurements made at 25° C. or room temperature, unless otherwise designated. All percentages are on a weight/weight basis.

As used herein the term "dermatological composition" refers to a composition useful for topical application to the skin of a human.

As used herein, the term "topical application" means to apply or spread the compositions to the surface of the skin.

As used herein, the term "cosmetically acceptable" means that the compositions or components thereof so described are of sufficiently high purity and suitable for use in contact with human skin without undue toxicity, incompatibility, instability, allergic response, and the like.

As used herein, the term "solution" refers to a liquid mixture.

As used herein the word "treat," "treating" or "treatment" refers to using the compositions of the present disclosure prophylactically to prevent outbreaks of undesirable dermatological symptoms, or therapeutically to ameliorate an existing undesirable dermatological condition, and/or extend the duration of the aesthetic benefit of a chemical peel procedure, or reduce the frequency of repeated chemical peel procedures.

As used herein the word "substantially pure" refers to a composition or preparation that is substantially free of other components, compositions or materials. For example, a substantially pure molecule, such as a retinoid derivative including retinol, can be at least 60%, at least 70%, at least 80%, at least 90% or at least 90%, by dry weight, of the retinoid derivative. Retinoid derivatives can be purified by standard chemical procedures, including partition chromatography, high performance liquid chromatography, thin layer chromatography and other procedures known in the art. Characterization and assay of retinoid derivative preparations and solutions including retinol solutions and preparations can be performed according to known procedures, including UV absorbance measurements and known procedures quantifying and characterizing retinoid preparations. See, e.g., USP (United States Pharmacopeia) standards and monograph procedures.

The term "effective amount", as used herein, means an amount sufficient to provide a cosmetic benefit following one or more treatments.

Provided herein is a method for exfoliation of skin, where the method comprises (a) cleansing skin to be exfoliated; (b) applying an acidic solution to the skin; and (c) applying an aqueous retinol solution to the skin after application of the acidic solution.

Provided herein is a method for exfoliation of skin, where the method comprises (a) cleansing skin to be exfoliated; (b) applying an acidic solution to the skin; and (c) applying an aqueous retinol solution to the skin after application of the acidic solution.

In one aspect, cleansing the skin is accomplished by applying an alcoholic solution, where the solution may contain, for example, isopropyl alcohol.

Acids that can be in the acidic solution of (b) include, but are not limited to, lactic acid, salicylic acid, resorcinol, glycolic acid, malic acid, mandalic acid, citric acid, Trichloroacetic acid (TCA), phenol, tartaric acid, or a combination thereof. In one non-limiting example, an acidic solution comprises lactic acid, salicylic acid, and resorcinol. The acidic solution can further include Isoceteth-20, Panthenol, or a combination thereof. In one embodiment, the acidic solution may further comprise one or more adjuvants.

In one aspect, the solution of (c) can contain retinol in a concentration of at least 1%, at least 2%, at least 3%, at least 4%, at least 5%, at least 6%, at least 7%, at least 8%, at least 9%, at least 10% or more. In other embodiments, the solution of (c) can contain retinol in a concentration of between about 1% to about 3%, between about 1% to about 5%, between about 1% to about 10%, between about 2% to about 5%, between about 2% to about 10%, between about 2% to about 6%, between about 2% to about 8%, between about 3% to about 5%, between about 3% to about 10%, between about 3% to about 6%, between about 3% to about 8%, between about 4% to about 6%, or between about 4% to about 10%. In one embodiment, the solution contains retinol in a concentration of about 5% in the solution. In another embodiment, the solution contains retinol in a concentration of about 3% in the solution. Retinol solutions may be substantially free of a surfactant and/or a stabilizer. For example, the solution may contain less than 1% of a surfactant and/or stabilizer. In some embodiments, the solution of (c) may include retinol derivatives. In other embodiments, the solution of (c) may include retinaldehyde, retinal, retinyl, palmitate, retinyl acetate and the like.

In one aspect of the method, the retinol solution may be applied to the skin about 3 minutes to about 1 week after applying the acidic solution. In one such method, the retinol solution is applied to the skin about 3 minutes after applying the acidic solution. In another method, the retinol is applied solution to the skin one or more times. For example, the solution may be applied every day for about 1 week.

The retinol solution of the present compositions is prepared from a substantially pure chemical powder source of retinol. In one embodiment, the retinol solution is substantially pure. In one embodiment, the purity of the retinol solution is at least about 99%, at least about 98%, at least about 97%, at least about 96%, at least about 95%, at least about 93%, at least about 90%, at least about 80%, at least about 70% or at least about 60%. In one embodiment, the purity of the retinol solution is at least about 98%. In some embodiments, the retinol solution is substantially free from retinol with a purity source of less than about 99%, less than about 98%, less than about 97%, less than about 96%, less than about 95%, less than about 93%, less than about 90%, less than about 80%, less than about 70% or less than about 60%.

In another embodiment, the retinol solution comprises retinol in a concentration of about 1%, about 2%, about 3%, about 4%, about 5%, about 6%, about 7%, about 8%, about 9%, about 10% or more. In other embodiments, the retinol solution comprises retinol in a concentration of between about 1% to about 3%, between about 1% to about 5%, between about 1% to about 10%, between about 2% to about 5%, between about 2% to about 10%, between about 2% to about 6%, between about 2% to about 8%, between about 3% to about 5%, between about 3% to about 10%, between about 3% to about 6%, between about 3% to about 8%, between about 4% to about 6%, or between about 4% to about 10%. In another embodiment, the retinol solution comprises retinol in a concentration of between about 3% and about 5%. In one embodiment, the retinol solution may further comprise one or more adjuvants.

In other aspect of the method, at least about 10%, at least about 15%, at least about 20%, at least about 25%, at least about 30%, at least about 40%, at least about 50%, at least about 60%, at least about 70%, at least about 80%, or at least about 90% of the treated skin is exfoliated.

In the present methods, a very superficial (exfoliation) peel thins and/or removes the stratum corneum and does not extend below the stratum granulosum. A superficial (epidermal) peel removes part of all of the epidermis from the stratum granulosum to the basal cell layer. A medium (papillary dermis) peel removes all of the epidermis and part or all of the papillary dermis. A deep (reticular dermis) peel removes the papillary dermis down to the upper portion of the reticular dermis.

In one aspect, the present method further comprise applying one or more of sunblock, moisturizer, emollient, antioxidant, astringents to the skin prior to the cleansing step or subsequent to application of the retinol solution.

Provided herein is a method for exfoliating skin, the method comprising cleansing skin to be exfoliated; applying an acidic solution to the skin; and applying a 3% retinol solution to the skin; wherein said retinol solution is applied to the skin after the acidic solution is applied to the skin.

Provided herein is a method for exfoliating skin, the method comprising cleansing skin to be exfoliated; applying an acidic solution to the skin; and applying a 3% retinol solution to the skin; wherein said retinol solution is applied to the skin after the acidic solution is applied to the skin and wherein said solution does not contain a surfactant or a stabilizer.

Provided herein is a method for exfoliating skin, the method comprising cleansing skin to be exfoliated; applying an acidic solution to the skin; and applying a 5% retinol solution to the skin; wherein said retinol solution is applied to the skin after the acidic solution is applied to the skin.

Provided herein is a method for exfoliating skin, the method comprising cleansing skin to be exfoliated; applying an acidic solution to the skin; and applying a 5% retinol solution to the skin; wherein said retinol solution is applied to the skin after the acidic solution is applied to the skin and wherein said solution does not contain a surfactant or a stabilizer.

Provided herein is a method for exfoliating skin, the method comprising cleansing skin to be exfoliated with an isopropyl alcohol solution; applying an acidic solution comprising lactic acid, salicylic acid, and resorcinol to the skin; and applying a 5% retinol solution to the skin; wherein said retinol solution is applied to the skin after the acidic solution is applied to the skin and wherein said solution does not contain a surfactant or a stabilizer. In one embodiment, the acidic solution further comprises Isoceteth-20 and/or Panthenol.

Provided herein is a method for exfoliating skin, the method comprising cleansing skin to be exfoliated with an isopropyl alcohol solution; applying an acidic solution comprising lactic acid, salicylic acid, and resorcinol to the skin; and applying a 5% retinol solution to the skin; wherein said retinol solution is applied to the skin after the acidic solution is applied to the skin and wherein said solution does not contain a surfactant or a stabilizer. In one embodiment, the acidic solution further comprises Isoceteth-20 and/or Panthenol.

Provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin. Also provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin. A benefit of the present exfoliation processes disclosed herein is that additional neutralization of skin is not required after application of the acidic solution. In one embodiment, the method improves overall photodamage. In another embodiment, the method improves fine lines and wrinkles. In yet another embodiment, the method improves skin tone unevenness. Improvement in skin after treatment with retinols as described herein in such methods can be, for example, at least 1.5 fold, at least 2-fold, at least 3-fold, at least 4-fold, at least 5-fold or more compared to untreated skin. Improvement in skin after treatment with retinols as described herein in such methods can be, for example, at least 1.5 fold or at least 2-fold compared to treatment methods with Retinoic Acid.

Also provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin. A benefit of the present exfoliation processes disclosed herein is that additional neutralization of skin is not required after application of the acidic solution. In one embodiment, the method improves overall photodamage. In another embodiment, the method improves fine lines and wrinkles. In yet another embodiment, the method improves skin tone unevenness. Improvement in skin after treatment with retinol as described herein in such methods can be, for example, at least 1.5 fold, at least 2-fold, at least 3-fold, at least 4-fold, at least 5-fold or more compared to untreated skin. Improvement in skin after treatment with retinol as described herein in such methods can be, for example, at least 1.5 fold or at least 2-fold compared to treatment methods with Retinoic Acid.

Provided herein is a method for exfoliation of skin, the method comprising cleansing skin to be exfoliated; applying an acidic solution to the skin; and applying about a 3% retinol solution to the skin; wherein the retinol solution is applied to the skin after the acidic solution is applied to the skin.

Provided herein is a method for exfoliation of skin, the method comprising cleansing skin to be exfoliated; applying an acidic solution to the skin; and applying about a 3% retinol solution to the skin; wherein the retinol solution is applied to the skin after the acidic solution is applied to the skin and wherein the solution does not contain a surfactant or a stabilizer.

Provided herein is a method for exfoliation of skin, the method comprising cleansing skin to be exfoliated; applying an acidic solution to the skin; and applying about a 5% retinol solution to the skin; wherein said retinol solution is applied to the skin after the acidic solution is applied to the skin.

Provided herein is a method for exfoliation of skin, the method comprising cleansing skin to be exfoliated; applying an acidic solution to the skin; and applying about a 5% retinol solution to the skin; wherein said retinol solution is applied to the skin after the acidic solution is applied to the skin and wherein said solution does not contain a surfactant or a stabilizer.

Provided herein is a method for exfoliation of skin, the method comprising cleansing skin to be exfoliated with an isopropyl alcohol solution; applying an acidic solution comprising lactic acid, salicylic acid, and resorcinol to the skin; and applying a 5% retinol solution to the skin; wherein said retinol solution is applied to the skin after the acidic solution is applied to the skin and wherein said solution does not contain a surfactant or a stabilizer. In one embodiment, the acidic solution further comprises isoceteth-20, Panthenol, denatured alcohol, or a combination thereof.

A composition for use in (b) of the skin exfoliation treatments described above may comprise one or more of lactic acid, salicylic acid, resorcinol, glycolic acid, malic acid, mandalic acid, citric acid, Trichloroacetic acid (TCA), phenol, tartaric acid, or a combination thereof. In one example, the acidic solution comprises a combination of lactic acid, salicylic acid, and resorcinol. The acidic solution may further comprise Isoceteth-20 and/or Panthenol (e.g., D-Panthenol).

A composition for use in (c) of the skin exfoliation treatments described above may comprise a carrier and a concentration of at least 1%, at least 2%, at least 3%, at least 4%, at least 5%, at least 6%, at least 7%, at least 8%, at least 9%, at least 10% or more of retinol. In other embodiments, the retinol solution comprises retinol in a concentration of between about 1% to about 3%, between about 1% to about 5%, between about 1% to about 10%, between about 2% to about 5%, between about 2% to about 10%, between about 2% to about 6%, between about 2% to about 8%, between about 3% to about 5%, between about 3% to about 10%, between about 3% to about 6%, between about 3% to about 8%, between about 4% to about 6%, or between about 4% to about 10%. For example, the composition contains a carrier and a concentration of about 3% or about 5% of a retinol. In one embodiment, the retinol is present in a concentration of about 3%. In another embodiment, the retinol is present in a concentration of about 5%. The retinol compositions may be prepared using a pure powder comprising a retinol.

In some embodiments, the solution of (c) may include retinol derivatives. In some embodiments, the solution of (c) may include retinaldehyde, retinal, retinyl, palmitate or retinyl acetate. Such solutions can be formulated without a stabilizer and/or a surfactant.

Compositions of the present methods are useful for a variety of chemical peels. Compositions may contain, in addition to the indicated components, a wide range of additional components. Such components include, without limitation, absorbents, antifoaming agents, antimicrobial agents, antioxidants, binders, biological additives, chelating agents (e.g., disodium EDTA, tetrasodium EDTA, sodium metasilicate, etc.), denaturants, external analgesics (e.g., aspirin, non-steroidal anti-inflammatories), steroidal anti-inflammatory drugs (such as hydrocortisone and the like), preservatives (e.g., imidazolidinyl urea, diazolidinyl urea, phenoxyethanol, methylparaben, ethylparaben, propylparaben, etc.), reducing agents, skin bleaching agents (e.g., hydroquinone, kojic acid, sodium metabisulfite, etc.), skin protectants, solubilizing agents, solvents, and thickening agents. Exceptions to these additional components are specifically noted below.

Provided herein are kits for exfoliating skin comprising a skin cleanser; an acidic solution; a retinol solution; and instructions for applying the solutions above, where the solutions are described supra. The kits may further include one or more of the additional components described supra. A kit may be packaged as single treatment packages or contain solutions and components sufficient for two or more treatments.

Pre-treatment Considerations

Pre-treatment regimens may improve skin characteristics in connection with the compositions and methods described herein.

A patient to be treated with the compositions and methods should avoid the following products and procedures: electrolysis, waxing, depilatory creams and laser hair removal. Patients who have had BOTOX® injections should wait until full effect of their treatment is seen before receiving a skin exfoliation treatment.

Three days before a skin exfoliation treatment, a patient should avoid the following products and procedures: Retin-A®, Renova®, Differin®, Tazorac®, any product containing retinol, AHA or BHA, or benzoyl peroxide, and any exfoliating products that may be drying or irritating. The use of these products/treatments prior to the peel may increase skin sensitivity and cause stronger reaction.

Contraindications for receiving a skin exfoliation treatment with the subject compositions and methods include, for example: active cold sores, herpes simplex or warts in the area to be treated, wounded, sunburned, excessively sensitive skin, dermatitis and inflammatory rosacea, use of Accutane® within the last year, a history of chemotherapy or radiation therapy, patients with history of allergies (especially allergies to salicylates like aspirin), rashes, or other skin reactions, or those who may be sensitive to any of the components in this treatment, pregnancy or active breast-feeding, patients with vitiligo, and patients with history of an autoimmune disease (such as rheumatoid arthritis, psoriasis, lupus, multiple sclerosis, etc.) or any condition that may weaken their immune system. Patients who have had medical cosmetic facial treatments or procedures (e.g., laser therapy, surgical procedures, cosmetic filler, micro dermabrasion, etc.) should wait until skin sensitivity completely resolves before receiving a very superficial or superficial peel.

Preparatory Compositions

A preparatory cleanser solution is to be prepared for application to skin in amounts that provide the benefit to the skin of the user, such as in an amount sufficient to remove dirt and oil from the skin. Cleansing solutions include, but are not limited to, alcohol solutions and are typically soap-free and include water, detergent, surfactant, humectants, skin conditioning agent, pH adjustor, extracts, preservatives, fragrance and colorant, however, any cleaner suitable for removing dirt and oil from skin may be used. In one embodiment, a cleansing solution comprises an alcohol solution. An exemplary, non-limiting alcohol solution comprises isopropyl alcohol, water/aqua, and acetone.

Peeling Solution

Various skin-renewal stimulating acids may be combined together, and tests can be used to evaluate their efficacy and side effects, for incorporation into cosmetics suitable for application to the skin.

Acids for use in the present compositions and methods are those with good, cosmetically acceptable characteristics, especially freedom from any unpleasant odor, low or substantially no toxicity, stability for shelf life, freedom from regulatory problems, known and tolerable side effects and a white or colorless appearance in the end product composition.

Preferred acids include, but are not limited to, lactic acid, salicylic acid, resorcinol, glycolic acid, malic acid, mandalic acid, citric acid, Trichloroacetic acid (TCA), phenol, tartaric acid, and the like.

Lactic acid is frequently used, alone or in combination with other acids for light and medium skin peels. It is sufficiently gentle to extend the results of a deeper peel. The lactic acid of the compositions useful herein is present in a concentration from about 5% to about 80%. In one embodiment, lactic acid of the compositions useful herein is present in a concentration of about 12%.

Salicylic acid, also known as 2-hydroxybenzoic acid, is a white crystalline powder having a melting point from about 157° to 159° C. See THE MERCK INDEX, Twelfth Edition, entry 8484, p. 1433 (1996), incorporated herein by reference. The salicylic acid of the compositions useful herein is present in a concentration from about 10% to about 50%. In one embodiment, salicylic acid of the compositions useful herein is present in a concentration of about 12%.

Resorcinol (resorcin; $C_6H_4(OH)_2$) a dihydroxy benzene. The resorcinol of the compositions useful herein is present in a concentration from about 5% to about 60%. In one embodiment, resorcinol of the compositions useful herein is present in a concentration of about 10%.

Glycolic acid is a gentle acid that dissolves bonds between skin cells. The glycolic acid of the compositions useful herein is present in a concentration from about 5% to about 70%. In one embodiment, glycolic acid of the compositions useful herein is present in a concentration of about 10%.

Malic acid, mandalic acid, citric acid, Trichloroacetic acid (TCA), phenol and tartaric acid are other examples of acids that can be used in the present compositions. Each of these acids may be present in a concentration from about 2% to about 80%. In one embodiment, each of these acids may be present in a concentration of about 10%.

In one aspect, the acidic solution comprises a combination of lactic acid, salicylic acid and resorcinol.

The pH of the formulation can be adjusted to optimize the availability of the acid and the stability of the formulation. A low pH is typically utilized in order to suppress ionization and enhance the penetration of the acid into the stratum corneum. The pH range may be between about 2.5 and about 4, or between about 3 and about 4.

A wide variety of acids, bases, and buffers may be utilized to adjust and/or maintain the pH of the compositions useful in the present methods. Examples of materials useful for adjusting and/or maintaining the pH include, without limitation, ammonia, sodium carbonate, sodium hydroxide, triethanolamine, hydrochloric acid, phosphoric acid, sodium hydrogen phosphate, sodium dihydrogen phosphate, citric acid, and the like.

These ingredients are present in a safe and effective amount in a topical cosmetically acceptable carrier, which can be of a variety of different forms.

The pharmaceutically-acceptable topical carrier, in total, typically comprises from about 0.1% to about 95% by weight of the composition of step one above, from about 70% to about 91%, or from about 80% to about 90%.

In one aspect, the acidic solution further comprises isoceteth-20. Isoceteth-20 is the polyethylene glycol ether of isocetyl alcohol and is used in cosmetic applications as an emulsifier and surfactant. The inventors found that inclusion of isoceteth-20 increases the spreading of the acids across the skin during application. In another aspect, the acidic solution further comprises panthenol.

In one aspect, a very superficial peel acidic solution contains:

| Material Description (Supplier) | % W/W |
| --- | --- |
| Alcohol SDA 40-2 190 Proof (Remet Corp.) | 77.750 |
| Salicylic Acid Crystals USP (Rona/EMD Industries, Inc.) | 7.000 |
| Resorcinol Crystals USP | 7.000 |
| Panthenol D1 Cosmetic (BASF) | 1.000 |
| Isoceteth-20 (Arlasolve ™) 200L (Croda, Inc.) | 0.250 |
| Lactic Acid **88% (RITA Corp.) | 7.000 |

In another aspect, a superficial peel acidic solution contains:

| Material Description (Supplier) | % W/W |
| --- | --- |
| Alcohol SDA 40-2 190 Proof (Remet Corp.) | 63 |
| Salicylic Acid Crystals USP (Spectrum Chemical) | 12 |
| Resorcinol Crystalline Powder, USP (Spectrum Chemical) | 10 |
| Lactic Acid 88% FCC (ADM) | 12 |
| D-Panthenol (DSM Nutritional Products) | 2 |
| Isoceteth-20 (Arlasolve ™) 200L (Uniqema/Croda, Inc.) | 1 |

Retinol Compositions

Retinoic Acid helps accelerate the exfoliation; get overall collagen and extracellular matrix build-up after application of the acidic solution to the skin. The Retinoic Acid solutions that have previously been used in chemical peel treatments are problematic in that they require a prescription having a concentration of 0.3% Retinoic Acid. More importantly, the prescriptions were found to not have a consistent amount of 0.3% Retinoic Acid and caused irritation following treatment.

In contrast, the inventors of the present application recognized that retinol solutions offered an improved alternative to Retinoic Acid preparations. Moreover, the present inventors identified that commercially available retinol solutions are not suitable for use in skin exfoliation treatments. Rather, making the solution from pure powder allowed for significantly better results.

Retinol solutions are to be prepared directly from a substantially pure chemical powder in a concentration of at least 3% or at least 5%. In one embodiment, a retinol solution has a purity of at least about 99%, at least about 98% or at least about 95%, and a concentration of at least 3% or at least 5%. In yet another embodiment, a retinol solution has a concentration of at least 1%, at least 2%, at least 3%, at least 4%, at least 5%, at least 6%, at least 7%, at least 8%, at least 9%, at least 10%, or more. In other embodiments, the retinol solution has a concentration of between about 1% to about 3%, between about 1% to about 5%, between about 1% to about 10%, between about 2% to about 5%, between about 2% to about 10%, between about 2% to about 6%, between about 2% to about 8%, between about 3% to about 5%, between about 3% to about 10%, between about 3% to about 6%, between about 3% to about 8%, between about 4% to about 6%, or between about 4% to about 10%.

A representative superficial peel solution (% W/W) contains 5% retinol crystals (Palm Pharmaceuticals, Inc.) dissolved in 95% SD Alcohol SDA 40-2 (200 proof; Remet Corp.).

A representative very superficial peel solution (% W/W) contains 3% retinol crystals (Palm Pharmaceuticals, Inc.) dissolved in 97% SD Alcohol SDA 40-2 (200 proof; Remet Corp.).

One in this field would understand that various concentrations of retinol solutions can be formulated based on the skin condition to be treated and the depth of skin to be penetrated.

In one aspect, the retinol solutions do not contain a stabilizer or a surfactant. Thus, in one example, a representative superficial peel solution (% W/W) contains 5% retinol crystals (Palm Pharmaceuticals, Inc.) dissolved in 95% SD Alcohol SDA 40-2 (200 proof; Remet Corp.), and does not contain a stabilizer or a surfactant. In another example, a representative very superficial peel solution (% W/W) contains 3% retinol crystals (Palm Pharmaceuticals, Inc.) dissolved in 97% SD Alcohol SDA 40-2 (200 proof; Remet Corp.), and does not contain a stabilizer or a surfactant.

Protective Post-peel Compositions

Skin improvement may be slowed or worsened by sunrays which may cause pigmentation and dryness. Accordingly, protective compositions are one class of supplementary compositions that optionally may be combined with the corrective compositions in the treatment regimens of the present disclosure to alleviate sun damage or dryness.

Suitable protective compositions include any composition capable of reducing skin damage, darkening, or dryness. In embodiments, protective compositions include sun block to screen out ultraviolet light rays. In embodiments, suitable protective compositions include creams are moisturizers formulated to help control dryness.

One suitable commercially available protective composition is Environmental Defense Sunscreen™ SPF 30+. This protective composition provides broad-spectrum sun protection and can advantageously be applied as part of a treatment regimen in accordance with this disclosure.

Kits

Provided herein are kits for exfoliating skin comprising: a skin cleanser; an acidic solution; a retinol solution; and instructions for applying solutions, wherein each of the kit components has been described supra.

Protocols for inclusion in the instructions include those, for example, described below in the examples.

Kits may also include one or more boxes or containers for each of the composition components, individually, or together, materials for mixing solutions, a headband or surgical cap, surgical gloves, small cotton gauze pads (3"× 3"), moisturizer to protect sensitive facial areas, small hand held fan (optional), and SkinMedica Environmental Defense Sunscreen™ SPF 30.

Kits may also be labeled for skin exfoliation.

Method of Use

The present disclosure also relates to a method for exfoliating skin aging and improving the skin's appearance. Such a method comprises topically applying to the skin a pad or other means for delivering an effective amount of compositions described herein.

Provided herein is a method for exfoliation of skin, the method comprising: cleansing skin to be exfoliated; applying an acidic solution to the skin; and applying a retinol solution to the skin; wherein said retinol solution is applied to the skin after the acidic solution is applied to the skin. Also provided herein is a method for exfoliation of skin, the method comprising: cleansing skin to be exfoliated; applying an acidic solution to the skin; and applying a retinol solution to the skin; wherein said retinol solution is applied to the skin after the acidic solution is applied to the skin. One in this field of study would recognize that the timing of each application can be empirically determined to best treat the patient's specific skin condition.

Using the compositions, at least about 10%, at least about 15%, at least about 20%, at least about 25%, at least about 30%, at least about 40%, at least about 50%, at least about 60%, at least about 70%, at least about 80%, or at least about 90% of the treated skin is exfoliated. In one embodiment, all or part of the superficial dermis is exfoliated. In another embodiment, all or part of the epidermal is exfoliated.

Provided herein is a method for exfoliation of skin, the method comprising cleansing skin to be exfoliated; applying an acidic solution to the skin; and applying a 3% retinol solution to the skin; wherein the retinol solution is applied to the skin after the acidic solution is applied to the skin.

Provided herein is a method for exfoliation of skin, the method comprising cleansing skin to be exfoliated; applying an acidic solution to the skin; and applying a 3% retinol solution to the skin; wherein the retinol solution is applied to the skin after the acidic solution is applied to the skin and wherein the solution does not contain a surfactant or a stabilizer.

Provided herein is a method for exfoliation of skin, the method comprising cleansing skin to be exfoliated; applying an acidic solution to the skin; and applying a 5% retinol solution to the skin; wherein said retinol solution is applied to the skin after the acidic solution is applied to the skin.

Provided herein is a method for exfoliation of skin, the method comprising cleansing skin to be exfoliated; applying an acidic solution to the skin; and applying a 5% retinol solution to the skin; wherein said retinol solution is applied to the skin after the acidic solution is applied to the skin and wherein said solution does not contain a surfactant or a stabilizer.

Provided herein is a method for exfoliation of skin, the method comprising cleansing skin to be exfoliated with an isopropyl alcohol solution; applying an acidic solution comprising lactic acid, salicylic acid, and resorcinol to the skin; and applying a 3% retinol solution to the skin; wherein said retinol solution is applied to the skin after the acidic solution is applied to the skin and wherein said solution does not contain a surfactant or a stabilizer. In one embodiment, the acidic solution further comprises isoceteth-20, panthenol, denatured alcohol, or a combination thereof.

Provided herein is a method for exfoliation of skin, the method comprising cleansing skin to be exfoliated with an isopropyl alcohol solution; applying an acidic solution comprising lactic acid, salicylic acid, and resorcinol to the skin; and applying a 5% retinol solution to the skin; wherein said retinol solution is applied to the skin after the acidic solution is applied to the skin and wherein said solution does not contain a surfactant or a stabilizer. In one embodiment, the acidic solution further comprises isoceteth-20, panthenol, denatured alcohol, or a combination thereof.

Provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin.

Provided herein are methods of improving photodamage, improving fine lines and wrinkles, improving skin tone unevenness, and/or improving mottled pigmentation, the method comprising: cleansing skin to be exfoliated; applying an acidic solution to the skin; and applying a retinol solution to the skin; wherein said retinol solution is applied to the skin after the acidic solution is applied to the skin.

A benefit of the present exfoliation processes disclosed herein is that additional neutralization of skin is not required after application of the acidic solution. In one embodiment, the method improves overall photodamage. In another embodiment, the method improves fine lines and wrinkles. In yet another embodiment, the method improves skin tone unevenness. Improvement in skin after treatment with retinols as described herein in such methods can be, for example, at least 1.5 fold, at least 2-fold, at least 3-fold, at least 4-fold, at least 5-fold or more compared to untreated skin. Improvement in skin after treatment with retinols as described herein in such methods can be, for example, at least 1.5 fold or at least 2-fold compared to treatment methods with Retinoic Acid.

In such methods, retinol solutions can be applied once skin has dried after application of the acidic solution. Further, retinol solutions can be applied once, or more than one time following application of the acidic solution based upon the condition of the skin to be treated. For example, a retinol solution can be applied to the skin from about three minutes to about one week after application of the acidic solution. In one embodiment, a retinol solution is applied to the skin about three minutes after application of the acidic solution. In another embodiment, a retinol solution is applied to the skin about three minutes after application of the acidic solution and then every day for about one week.

In order that those skilled in the art may be better able to practice the compositions and methods described herein, the following example is given for illustration purposes.

EXAMPLES

The following supplies will be used in the skin exfoliation methods described herein: cleansing (prepping) solution (approximately 4 mL per treatment); one vial acidic peeling solution; plastic measuring cups; retinol 3% or 5% solution (approximately 3 mL per treatment prepared from substantially pure powder dissolved in alcohol); headband or surgical cap; surgical gloves; small cotton gauze pads (3"×3"); moisturizer to protect sensitive facial areas; small hand held fan (optional); and sunscreen (e.g., SkinMedica Environmental Defense Sunscreen™ SPF 30).

Example 1

Very Superficial Skin Exfoliation Protocol

Pre-treatment Instructions

One week prior to conducting a very superficial peel, patients should avoid the following products and/or procedures: electrolysis, waxing, depilatory creams, laser hair removal, and patients who have had BOTOX® injections should wait until full effect of their treatment is seen before receiving a very superficial peel.

Three days prior to conducting a very superficial peel, patients should avoid the following products and/or procedures: Retin-A®, Renova®, Differin®, Tazorac®, any products containing retinol, AHA or BHA, or benzoyl peroxide, as well as any exfoliating products that may be drying or irritating. The use of these products/treatments prior to a peel may increase skin sensitivity and cause stronger reaction.

Contraindications that indicate a patient should not receive a skin exfoliation procedure include, for example, active cold sores, herpes simplex or warts in the area to be treated, wounded, sunburned, excessively sensitive skin, dermatitis and inflammatory rosacea, Accutane® use within the last year, A history of chemotherapy or radiation therapy, patients with history of allergies (especially allergies to salicylates like aspirin), rashes, or other skin reactions, or those who may be sensitive to any of the components in this treatment, patients who are pregnant who are actively breast-feeding, patients with vitiligo, and patients with history of an autoimmune disease (such as rheumatoid arthritis, psoriasis, lupus, multiple sclerosis, etc.) or any condition that may weaken their immune system. Patients who have had medical cosmetic facial treatments or procedures (e.g., laser therapy, surgical procedures, cosmetic filler, micro dermabrasion, etc.) should wait until skin sensitivity fully resolves before receiving a skin exfoliation procedure.

Exfoliation/Peel Procedure

If a medical professional is conducting the procedure, an informed consent should be obtained prior to the procedure. The medical professional should also review all topical products and medications patient is currently using, make sure the patient has complied with all pre-treatment instructions, and carefully examine the skin before performing the procedure; if any areas of previous irritation are observed, the procedure should not be conducted on these areas.

For comfort and safety, the patient is placed in a reclining position with the head elevated about 45 degrees. Hair is covered with a headband or surgical cap. The medical professional should take care to protect sensitive areas: lips, corners of the mouth, crevices at the side of the nose and corners of the eyes with a small amount of petroleum jelly or any moisturizer.

The lot number and expiration date of the Cleansing/Prepping Solution, Acidic/Peeling Solution and retinol solution should be recorded in the patient chart in the event if an adverse reaction occurs.

Step 1: Cleansing/Prepping Solution

As discussed above, the cleansing (prepping solution) is prepared with isopropyl alcohol, water/aqua and acetone.

Prior to application of this solution, the skin should be checked to ensure that is completely dry as application of the solution to moist skin may cause a stronger reaction and an unpredictable outcome.

Approximately 4 mL of cleansing/prepping solution is poured into the measuring cup provided and the cup is placed on a solid surface to prevent spillage. The medical professional should dip folded gauze (3"×3") into the solution until saturated and cleanse the areas of the skin where the peel is to be applied. The solution is applied to the face in the following pattern: Forehead: From the hairline down starting from the center of the forehead towards the temples; Sides of the face and jaw line: From the hairline towards the center of the face; Nose: Down the center and to the sides of the nose; Chin: From the center and out in each direction; Above the upper lip: From the center and out in each direction (do not apply directly on the lips); and Neck and décolleté: If favorable tolerability is seen to initial facial procedure, the cleansing/prepping solution can be administered on the neck and décolleté. Since the skin on the neck is more sensitive than facial skin, the cleansing/prepping solution should only be applied to the sides of the neck (from ear lobe down), avoiding the throat area, using very light pressure and avoiding rubbing and pulling the skin.

Step 2: Acidic/Peeling Solution

Very Superficial acidic/peeling solution contains Alcohol Denat., Salicylic Acid, Lactic Acid, Resorcinol, Panthenol, Isoceteth-20 in the following amounts:

| Material Description (Supplier) | % W/W |
|---|---|
| Alcohol SDA 40-2 190 Proof (Remet Corp.) | 77.750 |
| Salicylic Acid Crystals USP (Rona/EMD Industries, Inc.) | 7.000 |
| Resorcinol Crystals USP | 7.000 |
| Panthenol D1 Cosmetic (BASF) | 1.000 |
| Isoceteth-20 (Arlasolve ™) 200L (Croda, Inc.) | 0.250 |
| Lactic Acid **88% (RITA Corp.) | 7.000 |

The medical professional should pour 4 mL of acidic/peeling solution into the measuring cup provided and place the cup on a solid surface to prevent spillage. Clean, folded gauze should be used to dip into solution and saturate about half of the material. The solution should be applied to the face in the same pattern described in applying the cleansing/prepping solution (step 1). The gauze is re-dampened with acidic/peeling solution before treating each section of the face. The medical professional should not apply acidic/peeling solution above the periorbital rim. Importantly, this solution should never be applied inside of the bony orbital rim (directly under the eyes). The solution rests on the face for 3-4 minutes. A patient may experience mild to moderate tingling, burning or warmth. A fan may be used to cool the face if necessary and the symptoms usually subside or become mild within 2-3 minutes. If this is the patient's first very superficial skin exfoliation procedure or if the patient has thin, fragile or sensitive skin, only one layer of acidic/peeling solution should be applied. If the patient has received very superficial skin exfoliation procedures previously, and has tolerated the first layer of acidic/peeling solution well, a second application of the solution may be applied. The medical professional should wait one to three minutes prior to the second application. This allows time to check for excessive redness or any "frosting," which are white patches on the skin. If "frosting" or excessive redness is present, a second layer should not be applied. For those patients that require more aggressive treatment such as those with severe sun damage or acne, a third pass of acidic/peeling solution may be applied.

If step 1 was applied on the neck and décolleté, additional acidic/peeling solution may be used and the application expanded to the entire treated area. Application of the acidic/peeling solution to the neck and décolleté should be limited to one coat. The very superficial skin exfoliation procedure should be applied only to the sides of the neck (from ear lobe down), avoiding the throat area. Very light pressure should be used rubbing and pulling the skin should be avoided. Since the skin on the neck is more sensitive than facial skin, erythema might last slightly longer.

The acidic/peeling solution is self-neutralizing and does not require neutralization; rinsing is not necessary. In case of severe burning sensation, erythema and/or itching during the procedure the solution may be washed off with cool water.

Step 3: Retinol Solution

A very superficial retinol solution (% W/W) is prepared by mixing 3% retinol crystals (Palm Pharmaceuticals, Inc.) with 97% SD Alcohol SDA 40-2 (200 proof; Remet Corp.).

After a brief, 3-4 minute cooling-off period for the skin following step 2, the retinol solution can be applied. The medical professional should carefully pour approximately 3 mL into a measuring cup, and using fresh gauze, apply the solution to the skin in the pattern described in the previous steps. On areas where excessive burning, redness or "frosting" occurred with application of step 2, application of retinol should be avoided. Importantly, no pressure should be used when applying the retinol solution. Care should be taken to not work the solution into the crevices at the sides of the nose or corners of the mouth as the solution spreads easily and will be naturally absorbed into these areas. The retinol solution should not be applied above the periorbital rim and never applied inside of the bony orbital rim (directly under the eyes) or on the lips. Upon completion of this step, the patient's skin may have a slight yellowish tinge. This is normal and discoloration will typically resolve in 1-2 hours. The yellow tinge should not be washed off the face. At this point the skin may feel warm and tingly.

If a very superficial peel was applied on the neck and décolleté additional retinol should be used and expanded application to the entire treated area should be conducted. The retinol solution should only be applied to the sides of the neck (from ear lobe down), avoiding the throat area while avoiding any pressure during application of the retinol solution to the neck and décolleté.

Step 4: Sun Protection

Following application of Step 3, a generous amount of 30+ sunscreen (e.g., Environmental Defense Sunscreen™ SPF 30+) is applied to the entire face. If the neck and décolleté were treated, application is expanded to those areas.

Some patients may experience a slight increase in tingling or burning immediately following application of sunscreen, but these symptoms should not last longer than few minutes. A patient should take extra precautions to avoid sun exposure following the exfoliation procedure for at least one week after the procedure is performed.

Step 5: Post-Procedure Instructions and Considerations

Since retinol solution is used as part of the treatment, the skin will have a light yellow tinge immediately after the procedure; this is temporary and will typically fade in 1 to 2 hours. Patients should wait until after the yellow tinge completely disappears (1 to 2 hours) before washing the face or wait until the evening.

It is imperative for patients to use a sunscreen with an SPF of at least 30 and avoid direct sunlight for at least 1 week. Patients with hypersensitivity to the sun should take extra precautions to guard against exposure immediately following the procedure as they may be more sensitive following the peel. The skin will likely be more red than usual for 2-3 days and patients should avoid strenuous exercise during this time.

Approximately 48 hours after the treatment, the skin will start to peel. This peeling will generally last 2 to 3 days and a patient should take care not to pick or pull the skin. When washing the face, patients should not scrub or not use a wash cloth. A gentle cleanser that does not contain soap (e.g., SkinMedica Sensitive Skin Cleanser) is to be used.

While the skin is peeling, a patient should apply moisturizer recommended by a medical professional (e.g., SkinMedica Ultra Sheer Moisturizer) as often as needed to relieve any dryness.

Patient may resume the regular use of Retin-A, alpha hydroxy acid (AHA) products or bleaching creams only after the peeling process is complete. Patient should wait until peeling completely subsides before having any other facial procedure, including, but not limited to: facials, microdermabrasion, laser treatments (including laser hair removal), facial hair removal, BOTOX® injections, and injectable fillers.

If any redness or discoloration occurs after the peel, it can easily be covered with makeup and most activities can be resumed right away.

The procedure can be repeated every 3-4 weeks until desired results are achieved. Results are cumulative and maximum benefits are seen with a series of three or more peels.

Example 2

Superficial Skin Exfoliation Protocol

Pre-treatment instructions and exfoliation/peel procedures are as described above in Example 1. Superficial skin exfoliation protocols, in most cases, provide a patient with a deeper exfoliation.

Step 1: Cleansing/Prepping Solution

As discussed above, the cleansing (prepping solution) is prepared with isopropyl alcohol, water/aqua and acetone.

Prior to application of this solution, the skin should be checked to ensure that is completely dry as application of the solution to moist skin may cause a stronger reaction and an unpredictable outcome.

Approximately 4 mL of cleansing/prepping solution is poured into the measuring cup provided and the cup is placed on a solid surface to prevent spillage. The medical professional should dip folded gauze (3"×3") into the solution until saturated and cleanse the areas of the skin where the peel is to be applied. The solution is applied to the face in the following pattern: Forehead: From the hairline down starting from the center of the forehead towards the temples; Sides of the face and jaw line: From the hairline towards the center of the face; Nose: Down the center and to the sides of the nose; Chin: From the center and out in each direction; Above the upper lip: From the center and out in each direction (do not apply directly on the lips); Neck and décolleté: If favorable tolerability is seen to initial facial procedure, the cleansing/prepping solution can be administered on the neck and décolleté. Since the skin on the neck is more sensitive than facial skin, the cleansing/prepping solution should only be applied to the sides of the neck (from ear lobe down), avoiding the throat area, using very light pressure and avoiding rubbing and pulling the skin.

Step 2: Acidic/Peeling Solution

Superficial acidic/peeling solution contains Alcohol Denat., Salicylic Acid, Lactic Acid, Resorcinol, Panthenol, Isoceteth-20 in the following amounts:

| Material Description (Supplier) | % W/W |
| --- | --- |
| Alcohol SDA 40-2 190 Proof (Remet Corp.) | 63 |
| Salicylic Acid Crystals USP (Spectrum Chemical) | 12 |
| Resorcinol Crystalline Powder, USP (Spectrum Chemical) | 10 |
| Lactic Acid 88% FCC (ADM) | 12 |
| D-Panthenol (DSM Nutritional Products) | 2 |
| Isoceteth-20 (Arlasolve ™) 200L (Uniqema/Croda, Inc.) | 1 |

The medical professional should pour 4 mL of acidic/peeling solution into the measuring cup provided and place the cup on a solid surface to prevent spillage. Clean, folded gauze should be used to dip into solution and saturate about half of the material. The solution should be applied to the face in the same pattern described in applying the cleansing/prepping solution (step 1). The gauze is re-dampened with acidic/peeling solution before treating each section of the face. The medical professional should not apply acidic/peeling solution above the periorbital rim. Importantly, this solution should never be applied inside of the bony orbital rim (directly under the eyes). The solution rests on the face for 3-4 minutes. A patient may experience mild to moderate tingling, burning or warmth. A fan may be used to cool the face if necessary and the symptoms usually subside or become mild within 2-3 minutes. If this is the patient's first superficial skin exfoliation procedure or if the patient has thin, fragile or sensitive skin, only one layer of acidic/peeling solution should be applied. If the patient has received superficial skin exfoliation procedures previously, and has tolerated the first layer of acidic/peeling solution well, a second application of the solution may be applied. The medical professional should wait one to three minutes prior to the second application. This allows time to check for excessive redness or any "frosting," which are white patches on the skin. If "frosting" or excessive redness is present, a second layer should not be applied. For those patients that require more aggressive treatment, such as those with severe sun damage or acne, a third pass of acidic/peeling solution may be applied.

If step 1 was applied on the neck and décolleté, additional acidic/peeling solution may be used and the application expanded to the entire treated area. Application of the acidic/peeling solution to the neck and décolleté should be limited to one coat. The superficial skin exfoliation procedure should be applied only to the sides of the neck (from ear lobe down), avoiding the throat area. Very light pressure should be used rubbing and pulling the skin should be avoided. Since the skin on the neck is more sensitive than facial skin, erythema might last slightly longer.

The acidic/peeling solution is self-neutralizing and does not require neutralization; rinsing is not necessary. In case of severe burning sensation, erythema and/or itching during the procedure the solution may be washed off with cool water.

Step 3: Retinol Solution

A superficial retinol solution (% W/W) is prepared by mixing 5% retinol crystals (Palm Pharmaceuticals, Inc.) with 95% SD Alcohol SDA 40-2 (200 proof; Remet Corp.).

After a brief, 3-4 minute cooling-off period for the skin following step 2, the retinol solution can be applied. The medical professional should carefully pour approximately 3 mL into a measuring cup, and using fresh gauze, apply the solution to the skin in the pattern described in the previous steps. On areas where excessive burning, redness or "frosting" occurred with application of step 2, application of retinol should be avoided. Importantly, no pressure should be used when applying the retinol solution. Care should be taken to not work the solution into the crevices at the sides of the nose or corners of the mouth as the solution spreads easily and will be naturally absorbed into these areas. The retinol solution should not be applied above the periorbital rim and never applied inside of the bony orbital rim (directly under the eyes) or on the lips. Upon completion of this step, the patient's skin may have a slight yellowish tinge. This is normal and discoloration will typically resolve in 1-2 hours. The yellow tinge should not be washed off the face. At this point the skin may feel warm and tingly.

If a superficial peel was applied on the neck and décolleté additional retinol should be used and expanded application to the entire treated area should be conducted. The retinol solution should only be applied to the sides of the neck (from ear lobe down), avoiding the throat area while avoiding any pressure during application of the retinol solution to the neck and décolleté.

Step 4: Sun Protection

Following application of Step 3, a generous amount of 30+ SPF sunscreen (e.g., Environmental Defense Sunscreen™ SPF 30+) is applied to the entire face. If the neck and décolleté were treated, application is expanded to those areas.

Some patients may experience a slight increase in tingling or burning immediately following application of sunscreen, but these symptoms should not last longer than few minutes. A patient should take extra precautions to avoid sun exposure following the exfoliation procedure for at least one week after the procedure is performed.

Step 5: Post-Procedure Instructions and Considerations

Since retinol solution is used as part of the treatment, the skin will have a light yellow tinge immediately after the procedure; this is temporary and will typically fade in 1 to 2 hours. Patients should wait until after the yellow tinge completely disappears (1 to 2 hours) before washing the face or wait until the evening.

It is imperative for patients to use a sunscreen with an SPF of at least 30 and avoid direct sunlight for at least 1 week.

Patients with hypersensitivity to the sun should take extra precautions to guard against exposure immediately following the procedure as they may be more sensitive following the peel.

The skin will likely be more red than usual for 2-3 days and patients should avoid strenuous exercise during this time.

Approximately 48 hours after the treatment, the skin will start to peel. This peeling will generally last 2 to 3 days and a patient should take care not to pick or pull the skin.

When washing the face, patients should not scrub or not use a wash cloth. A gentle cleanser that does not contain soap (e.g., SkinMedica Sensitive Skin Cleanser) is to be used.

While the skin is peeling, a patient should apply moisturizer recommended by a medical professional (e.g., SkinMedica Ultra Sheer Moisturizer) as often as needed to relieve any dryness.

Patient may resume the regular use of Retin-A, alpha hydroxy acid (AHA) products or bleaching creams only after the peeling process is complete.

Patient should wait until peeling completely subsides before having any other facial procedure, including, but not limited to: facials, microdermabrasion, laser treatments (including laser hair removal), facial hair removal, BOTOX® injections, and injectable fillers.

If any redness or discoloration occurs after the peel, it can easily be covered with makeup and most activities can be resumed right away.

The procedure can be repeated every 3-4 weeks until desired results are achieved. Results are cumulative and maximum benefits are seen with a series of three or more peels.

Example 3

Patient Studies

Three studies have been conducted to test the use of Retinol as a replacement compound for Retinoic Acid. A concentration of 2% (w/w) Retinol was first tested and increased as needed. The first two studies established the formulation and dosages by comparing peeling and tolerability to Retinoic Acid 0.3%, when used with one exfoliation (peel) as described above in Examples 1 and 2. The third study compared efficacy and tolerability of the selected formula and dose to Retinoic Acid 0.3% when used with a series of three peel procedures.

Study 1: Retinol 2% vs. RA 0.3%

The objective of the study was to determine if retinol 2% was comparable to Retinoic Acid 0.3% in terms of peeling efficacy and tolerability.

The study design was a split-face, single-blind (patient) clinical study of a 7-day duration (visits at the center on day 0 for the initial treatment, on day 4 and day 7). There were 10 patients (N=10) and subjects were aged 18-65 years having Fitzpatrick Skin Types I-IV.

Treatments were as follows:
1. One very superficial peel (prepping and peeling) full face.
2. Left Side: 2 cc Retinol 2%
3. Right Side: 2 cc Retinoic Acid 0.3%

Treatment protocols were as described in the Examples above.

Assessments were conducted by the investigator and subjects: peeling, erythema, burning/stinging, itching, and tightness were assessed. The investigator and subjects each assessed the left and right facial sides for peeling efficacy and selected one of the following choices:

LEFT SIDE: left side demonstrates more peeling than the right side.

RIGHT SIDE: right side demonstrates more peeling than the left side.

NO PREFERENCE: There is no discernable difference in the amount of peeling on either side; both sides peeled equally.

Subjects kept a daily diary for the week after receiving the peel. They graded the peeling on each side of their face using the following 5-point scale:

0=No Peeling: Skin is completely smooth with no evidence of peeling.

1=Minimal Peeling: Skin is smooth with rare areas of peeling/flaking.

2=Mild Peeling: Skin generally is smooth with a few areas of peeling/flaking.

3=Moderate Peeling: Noticeable peeling/flaking in several areas on the face.

4=Severe Peeling: Large flakes/sheets of skin peeling in several areas on the face.

Subjects also graded burning/stinging, itching and tightness on a 4-point scale.

The results of this study (investigator and subject assessments; peeling efficacy and tolerability) are provided in FIG. 1. Both the investigator and subject assessments demonstrated more peeling, stinging/burning and tightness on the Retinoic Acid-treated side of the face compared to the retinol-treated side.

Both the investigator and subject assessments demonstrated that retinol 2% is not a comparable percentage to Retinoic Acid 0.3% when used with the exfoliation process.

Study 2: Retinol 3% vs. RA 0.3%

The next study was conducted to determine the effect of increasing the percentage of retinol to 3.0% and comparing the results to Retinoic Acid 0.3%. The objective of this study was to determine the formula and percentage of retinol that is comparable to Retinoic Acid 0.3%, in terms of peeling efficacy and tolerability.

Treatments were as follows:
1. One very superficial peel (prepping and peeling) full face.
2. Left Side: 2 cc Retinol 3%
Oil Formula (N=20)
Oil-free Formula (N=6)
3. Right Side: 2 cc Retinoic Acid 0.3%

The study design was a split-face, single-blind (patient) clinical study of a 7-day duration (visits at the center on day 0 for the initial treatment, on day 4 and day 7). There were 26 patients (N=26) aged 18-65 years, and having Fitzpatrick Skin Types I-IV.

Assessments were conducted by the investigator and subjects: peeling, erythema, burning/stinging, itching, and tightness were assessed using the scoring system above. The investigator and subjects each assessed the left and right facial sides for peeling efficacy and selected one of the choices identified above.

Figure 2:
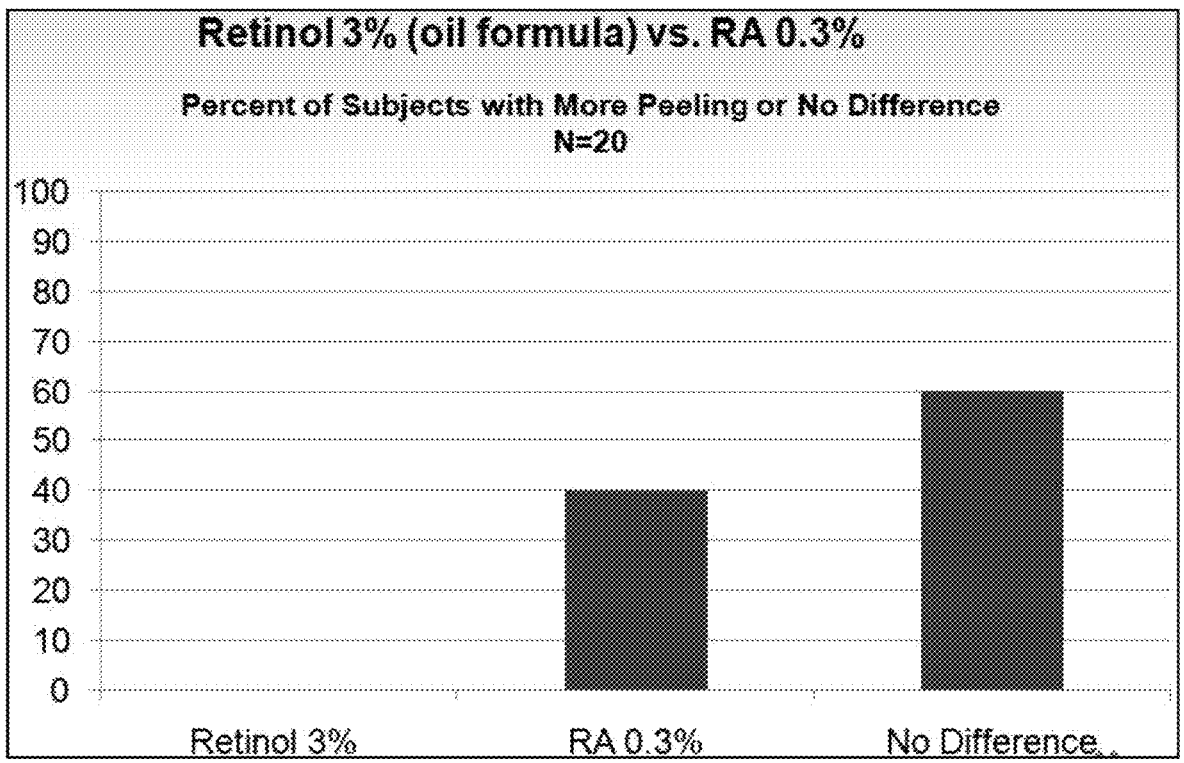
FIG. 2 illustrates the percentage of subjects from Study 2 exhibiting more peeling with retinol 3% (oil formula), Retinoic Acid 0.3% or no difference; results are shown as percentage of subjects preferring each indicated treatment or no difference.
Figure 3:
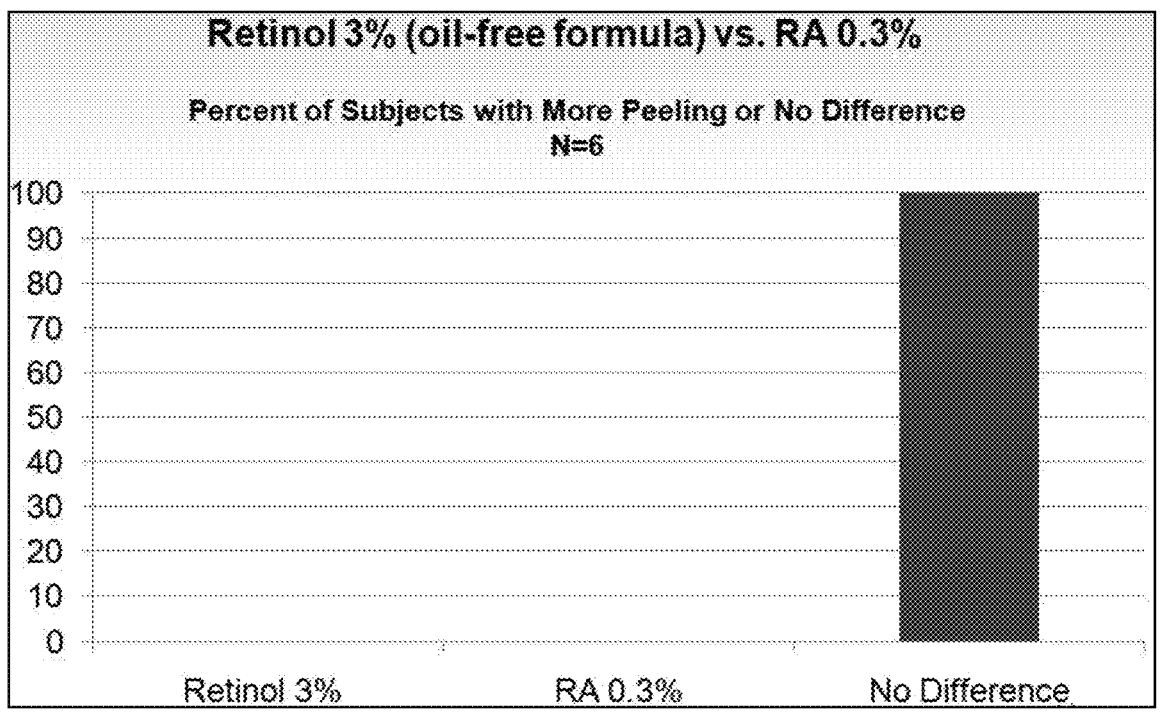
FIG. 3 illustrates the percentage of subjects from Study 2 exhibiting more peeling with retinol 3% (oil-free formula), Retinoic Acid 0.3% or no difference; results are shown as percentage of subjects preferring each indicated treatment or no difference.

The outcome of the assessments are shown in FIG. 2 (oil formula) and FIG. 3 (oil-free formula). Retinol 3.0% (oil-free formula) was found to demonstrate similar peeling efficacy and tolerability to Retinoic Acid 0.3%.

Study 3: Retinol 3% (Oil-Free) vs. RA 0.3%

The study step was conducted to determine if Retinol 3% in alcohol (i.e., oil-free) has comparable efficacy (improvements in photodamage, etc.), peeling efficacy and tolerability to Retinoic Acid 0.3% when used in a series of peels.

The objective of the study was to compare the tolerability and efficacy of Retinol 3% (oil-free) vs. Retinoic Acid 0.3% in subjects with mild to moderate photodamage when used with a series of three peel procedures.

The study design was a split-face, single-blind (patient) clinical study of a 3-month study duration (initial treatment, day 5, week 4, week 4+5 days, week 8, week 8+5 days, final visit 2 weeks post-week 8). There were 20 subjects (N=20) aged 18-65 years having Fitzpatrick Skin Types I-IV. Patients had mild to moderate photodamage (wrinkles, hyperpigmentation, acne or acne scarring).

Treatments were as follows:
One very superficial peel (prepping and peeling) full face.
Left Side: 2 cc Retinol 3% (oil-free)
Right Side: 2 cc Retinoic Acid 0.3%

Assessments were conducted by the investigator and subjects: efficacy (i.e., photodamage and peeling) and tolerability (i.e., erythema, burning/stinging, itching, tightness) using the scoring system above.

Both investigator and subjects assessed the left and right facial sides for peeling efficacy and selected one of the following choices:
  LEFT SIDE: Left side demonstrates more peeling than the right side; left side also demonstrates more improvement in photodamage.
  RIGHT SIDE: Right side demonstrates more peeling than the left side; right side also demonstrates more improvement in photodamage.
  NO PREFERENCE: There is no discernable difference in the amount of peeling on either side; both sides peeled equally. Both sides improved equally in the appearance of photodamage.

The results of this study are presented in FIGS. 4-7.

Figure 4:
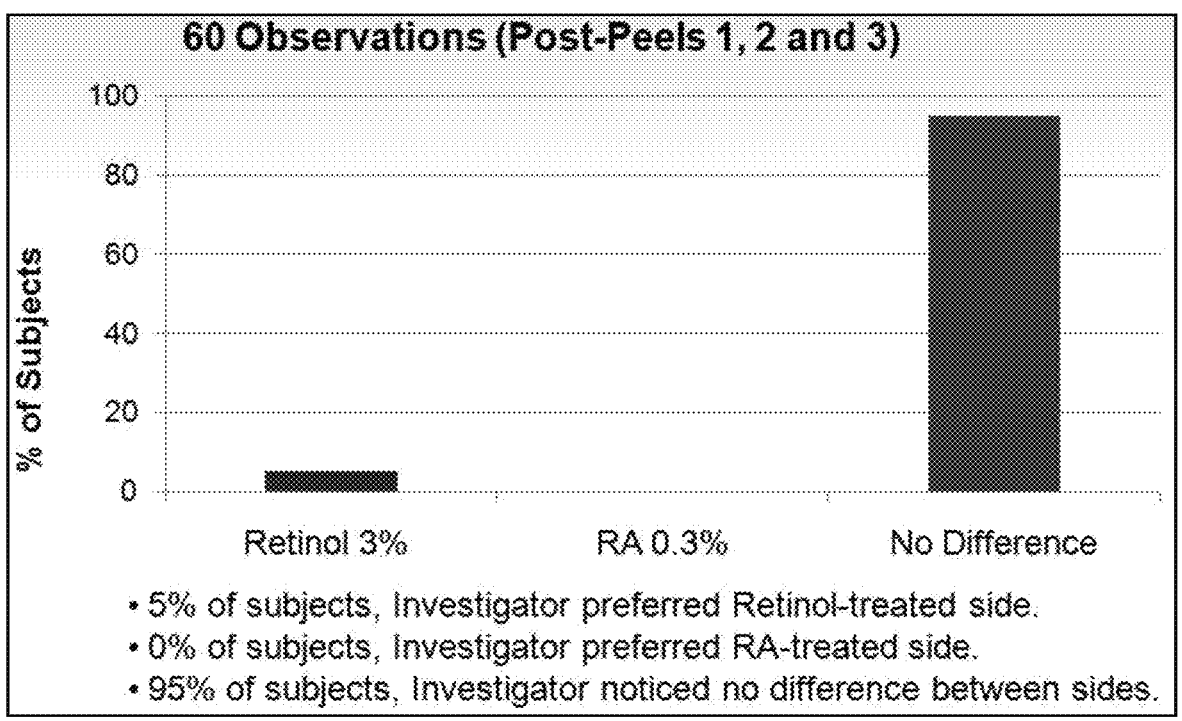
FIG. 4 illustrates the results of 60 observations by investigators and subjects (post-peels 1, 2 and 3 of Study 3) of treatment of patients with retinol 3% compared to Retinoic Acid 0.3%. Results are shown as percentage of subjects preferring each indicated treatment or no difference.

As illustrated in FIG. 4, the investigator preferred the retinol-treated side in 5% of subjects; the investigator preferred the Retinoic Acid-treated side 0% of subjects; and the investigator noticed no difference between the sides in 95% of subjects.

Figure 5:
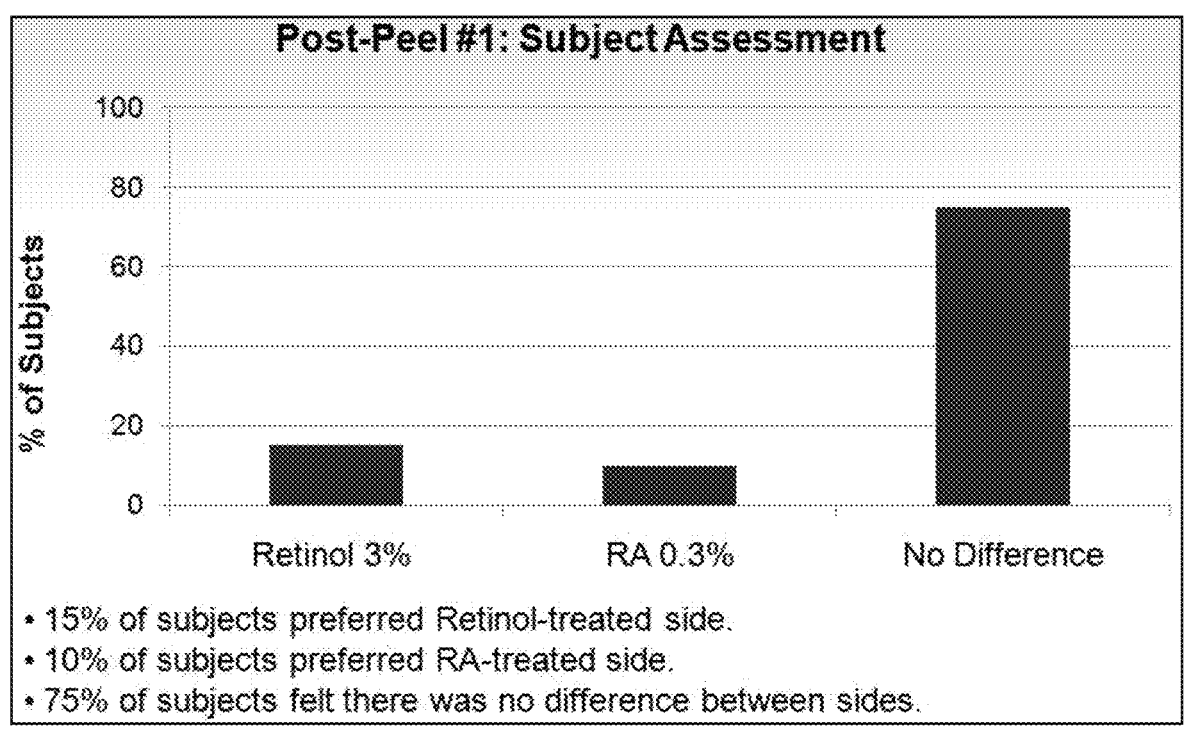
FIG. 5 provides the results of the post-peel #1 subject assessment. Results are shown as percentage of subjects preferring each indicated treatment or no difference.

FIG. 5 provides the results of the post-peel #1 subject assessment: 15% of subjects preferred the retinol-treated side; 10% of subjects preferred the Retinoic Acid-treated side; and 75% of subjects felt there was no difference between the sides.

Figure 6:
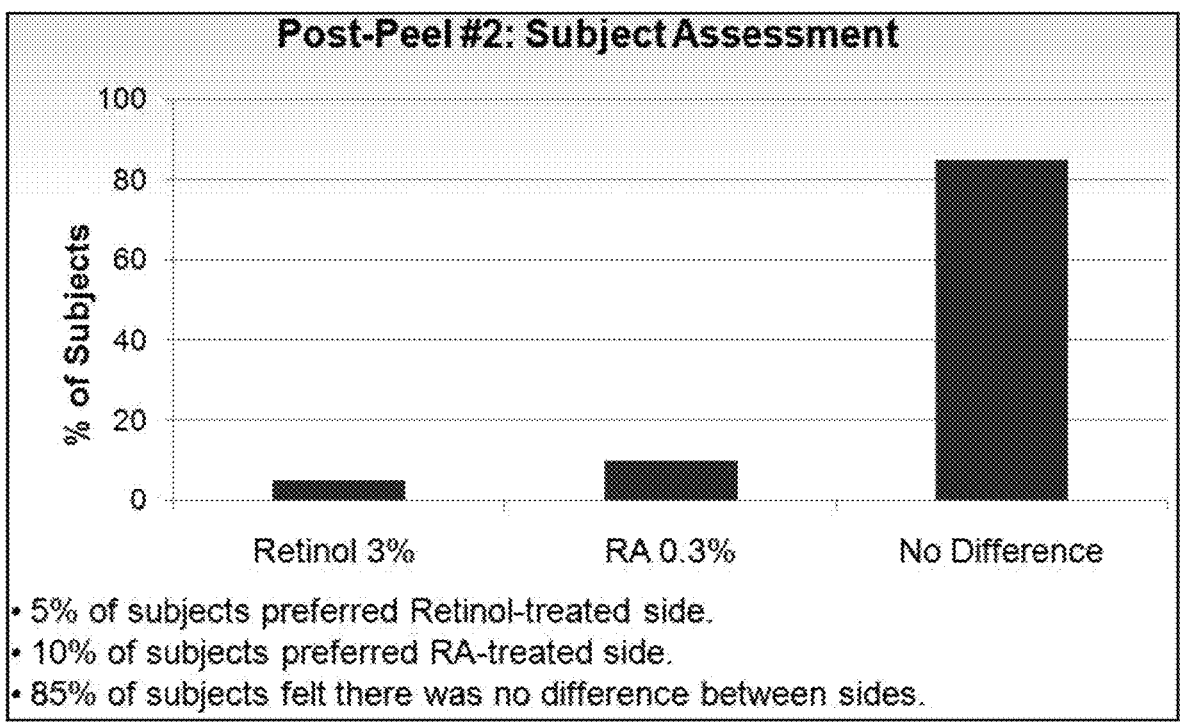
FIG. 6 provides the results of the post-peel #2 subject assessment. Results are shown as percentage of subjects preferring each indicated treatment or no difference.

FIG. 6 provides the results of the post-peel #2 subject assessment: 5% of subjects preferred the retinol-treated side; 10% of subjects preferred the Retinoic Acid-treated side; and 85% of subjects felt there was no difference between the sides.

Figure 7:
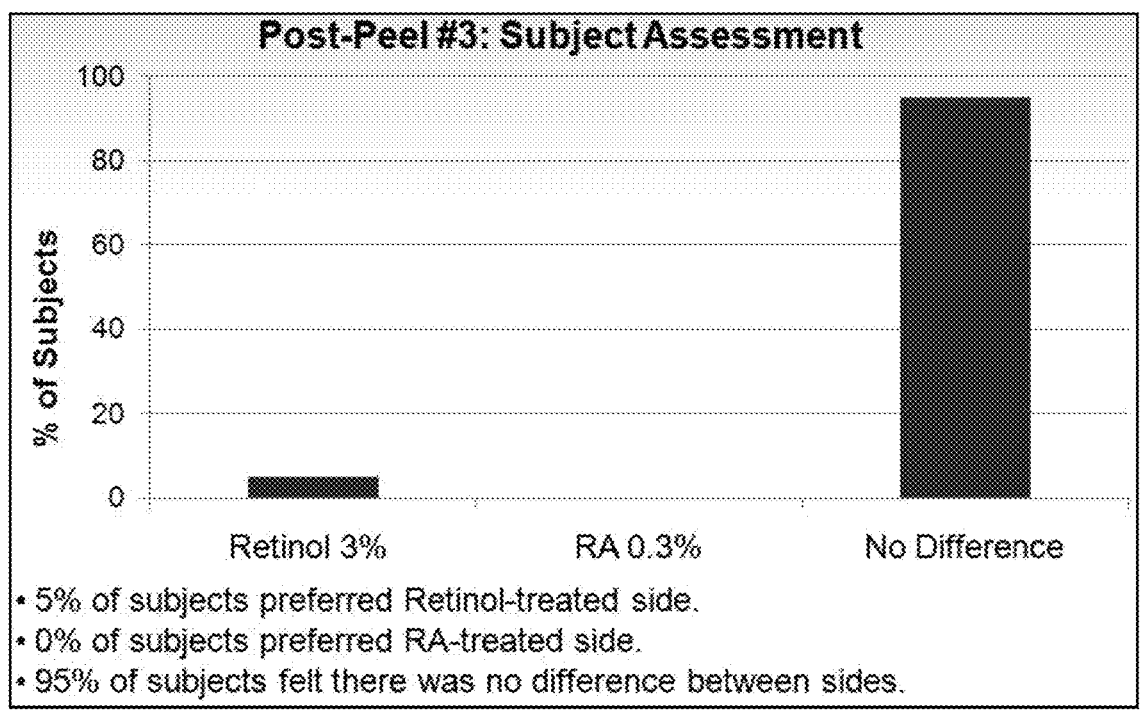
FIG. 7 provides the results of the post-peel #3 subject assessment. Results are shown as percentage of subjects preferring each indicated treatment or no difference.

FIG. 7 provides the results of the post-peel #3 subject assessment: 5% of subjects preferred the retinol-treated side; 0% of subjects preferred the Retinoic Acid-treated side; and 95% of subjects felt there was no difference between the sides.

In 95% of subjects, both investigator and subject assessments demonstrated no differences in efficacy (photodamage) and tolerability between the two sides at the end of treatment.

One subject (5%) demonstrated a difference favoring the Retinol-treated side. This subject developed irritation (rash, redness) on the retinol-treated side which was treated with topical hydrocortisone for 3 days at which time the irritation was resolved. The subject was re-challenged and did not experience a reaction.

FIG. 8 provides the results of an independent assessment of efficacy post-peel #3 based on blinded photograph evaluation by an expert physician. Retinol treatment produced about twice as much improvement in photodamage, fine lines and wrinkles and unevenness of skin tone as retinoic acid.

In conclusion, these studies showed that retinol 3% in ethanol demonstrates comparable peeling efficacy and tolerability to Retinoic Acid 0.3%. Retinol was found to produce superior efficacy as compared to Retinoic Acid with respect to improving overall photodamage, the appearance of fine lines and wrinkles, and skin tone unevenness. The superior results with respect to the effect of retinol on skin tone unevenness was statistically significant (p=0.037).

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A kit for exfoliating skin of a patient, the kit consisting of:
  a. a skin cleanser for removing dirt and oil from the skin of the patient, the skin cleanser consisting of isopropyl alcohol, water and acetone;
  b. an acidic solution for exfoliating the skin, the acidic solution consisting of an alcohol, salicylic acid, resorcinol, panthenol, isoceteth-20, and lactic acid;
  c. a retinol solution for accelerating the skin exfoliation, the retinol solution consisting of purified retinol in a concentration of about 3 wt % and a 200 proof denatured alcohol, the retinol solution having a purity of at least about 98%; and
  d. a plurality of measuring cups for measuring an amount of the skin cleanser,
    wherein the acidic solution and the retinol solution are topically applied sequentially to the skin of the patient.

* * * * *